(12) United States Patent
Lee et al.

(10) Patent No.: US 9,285,534 B2
(45) Date of Patent: Mar. 15, 2016

(54) FIBER-OPTIC SURFACE PLASMON RESONANCE SENSOR AND SENSING METHOD USING THE SAME

(75) Inventors: Kyeong Seok Lee, Seoul (KR); Won Mok Kim, Seoul (KR); Taek Sung Lee, Seoul (KR); In Ho Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 403 days.

(21) Appl. No.: 13/357,837

(22) Filed: Jan. 25, 2012

(65) Prior Publication Data
US 2013/0120752 A1 May 16, 2013

(30) Foreign Application Priority Data
Nov. 11, 2011 (KR) .......... 10-2011-0117414

(51) Int. Cl.
| | |
|---|---|
| G02B 6/00 | (2006.01) |
| G02F 1/035 | (2006.01) |
| G02B 6/02 | (2006.01) |
| G02B 5/00 | (2006.01) |
| G01N 21/552 | (2014.01) |
| G02B 6/122 | (2006.01) |

(52) U.S. Cl.
CPC *G02B 6/02* (2013.01); *G02B 5/008* (2013.01); *G01N 21/553* (2013.01); *G02B 6/1226* (2013.01)

(58) Field of Classification Search
CPC .............. G01N 21/553; G01N 21/554; G01N 21/7703; G02B 6/34; G02B 6/4214; G02B 6/30; G02B 6/132; G02B 6/02061; G01D 5/35383; G01D 5/353

USPC .............. 385/2, 8, 12, 27, 30, 39, 40, 49, 385/128–131, 141, 142, 144; 356/445, 451, 356/480
See application file for complete search history.

(56) References Cited

U.S. PATENT DOCUMENTS

| | | | |
|---|---|---|---|
| 5,067,788 A * | 11/1991 | Jannson et al. .................... 385/2 |
| 5,359,681 A | 10/1994 | Jorgenson et al. |
| 5,822,073 A * | 10/1998 | Yee et al. ....................... 356/445 |
| 5,991,048 A * | 11/1999 | Karlson et al. ................ 356/445 |
| 6,432,364 B1 * | 8/2002 | Negami et al. ............. 422/82.11 |
| 2007/0286546 A1 * | 12/2007 | Masson et al. .................. 385/12 |
| 2009/0253130 A1 * | 10/2009 | Yoo ................................. 435/6 |

(Continued)

OTHER PUBLICATIONS

Ahn, J.H., et al. "Side-polished fiber optic sensor based on waveguide coupled surface Plasmon resonance,"The 5th International Conference on Surface Plasmon Photonics, May 15-20, 2011, 4 pages.

*Primary Examiner* — Kaveh C Kianni
*Assistant Examiner* — Hung Lam
(74) *Attorney, Agent, or Firm* — NSIP Law

(57) ABSTRACT

A fiber-optic surface plasmon resonance sensor may include an optical fiber and a surface plasmon excitation layer. The optical fiber may include a core, a cladding surrounding the core, and a depression. The surface plasmon excitation layer may include a first excitation layer, a second excitation layer and an optical waveguide layer between the first excitation layer and the second excitation layer. Incident light incident through the core may be coupled to the surface plasmon excitation layer at a specific angle of incidence and wavelength satisfying the surface plasmon resonance condition. Depending on the polarizing direction of the incident light, an s-polarized component may be coupled to the guided-wave mode in the optical waveguide layer constituting the surface plasmon excitation layer.

24 Claims, 9 Drawing Sheets

(56) References Cited

U.S. PATENT DOCUMENTS

2010/0039648 A1* 2/2010 Garcia Da Fonseca ....... 356/445
2011/0157590 A1* 6/2011 Lee et al. ..................... 356/445
2011/0157593 A1* 6/2011 Miyadera et al. ............. 356/445

* cited by examiner

FIBER-OPTIC SURFACE PLASMON RESONANCE SENSOR AND SENSING METHOD USING THE SAME

CROSS-REFERENCE TO RELATED APPLICATIONS

This application claims priority under 35 U.S.C. §119 to Korean Patent Application No. 10-2011-117414, filed on Nov. 11, 2011, in the Korean Intellectual Property Office, the disclosure of which is incorporated herein by reference in its entirety.

BACKGROUND

1. Field

Embodiments relate to a fiber-optic surface plasmon resonance sensor and a sensing method using the same.

2. Description of the Related Art

A surface plasmon resonance sensor is a sensor utilizing the phenomenon that the excitation condition of surface plasmons, which are charge density waves of free electrons generated on the surface of a metal film at a metal-dielectric interface, is very sensitive to the change in surrounding environments. Biosensors and environmental sensors based on surface plasmon resonance are extensively studied.

The conventional surface plasmon resonance sensor has a structure including a prism with a high refractive index and a thin layer of a single metal on the basal plane of the prism. When p-polarized light is incident on the prism base with an angle larger than the angle of total internal reflection, surface plasmons are excited by the light incident at a specific angle satisfying the phase matching condition yielding a dip in the reflectance curve. The operation as sensor is achieved by measuring the change of the reflectance curve in response to change in surrounding medium on the surface of the metal film by various means. When monochromatic light is used, the change in the resonance angle at which the surface plasmons are excited may be measured or, with the angle of incidence fixed at the initial resonance angle, the change in the intensity or phase of the reflected light may be measured. When a polychromatic light source is used, the change in resonance wavelength for a particular angle of incidence may be monitored using a spectrometer to detect the change in the surrounding medium.

Such a prism coupler-based surface plasmon resonance sensor has high sensitivity and allows for label-free, real-time reaction analysis. On the other hand, since it requires a high-precision two-axis goniometer and a control system therefor, the cost is high and the system configuration is complicated and bulky. Accordingly, it is not suitable for point-of-care diagnosis or remote sensing.

The fiber-optic surface plasmon resonance sensor proposed in the early 1990s combines advantages from both the fiber-optic sensor appropriate for remote sensing with the high sensitivity of the surface plasmon resonance sensor. Due to the simple system configuration and low cost, it has attracted much attention. For example, U.S. Pat. No. 5,359,681 titled "Fiber optic sensor and methods and apparatus relating thereto" discloses a fiber-optic surface plasmon resonance sensor having a metal layer in contact with an exposed optical fiber core. However, the conventional fiber-optic surface plasmon resonance sensor has several problems.

FIG. 1 is a contour map showing a theoretical calculation result of light reflectance inside the core of a conventional fiber-optic surface plasmon resonance sensor as a function of internal incident angle and wavelength of incident light. The contour map shown in FIG. 1 shows a calculation result for a fiber-optic surface plasmon resonance sensor having a 45-nm thick gold (Au) thin film, which is in contact with a core made of silica, as a surface plasmon excitation layer. The medium surrounding the gold (Au) thin film was assumed to be water.

Since the fiber-optic surface plasmon resonance sensor includes no mechanical moving parts for satisfying the phase matching condition, the internal incident angle in the core is determined by the refractive index of the core and the numerical aperture of the optical fiber. In case of a core made of silica, the minimum acceptance angle of internal incidence, which corresponds to the angle of total internal reflection, for an optical fiber with a numerical aperture of 0.24 is about 80° and that for an optical fiber with a numerical aperture of 0.48 is about 71°.

Considering that the allowable numerical aperture of most of the currently commercially available fiber-optic based spectrometer is about 0.2, an internal incident angle between about 80° and 90° is realistic for the silica-based fiber-optic surface plasmon resonance sensor. Excluding the low incident angle range of impractical high numerical aperture, the surface plasmon resonance wavelength is maintained around 600 nm in spite of the change in the internal incident angle in broad ranges, as shown in FIG. 1. This suggests that the change in resonance wavelength is quite limited even when the multi-mode optical fiber with relatively large numerical aperture is used.

Accordingly, since the operation wavelength is determined by the refractive index of the medium to be analyzed, a light source whose wavelength deviates from the given operation wavelength region cannot be used. Especially, when a single-mode optical fiber is used, the sensor detects the change in signal intensity at a specific position on the reflectance dip curve. In this case, it is very difficult to fine-tune the resonance condition to optimize the signal intensity for the conventional fiber-optic surface plasmon resonance sensor.

In addition, in order to calibrate a signal fluctuation due to external noise factors such as the intensity fluctuation of light source, temperature increase of the measurement system, or the like, it is required to use an additional optical fiber for a reference channel or to form an additional cascade-type reference channel on the same optical fiber. Such requirements cause a burden in process.

SUMMARY

An aspect of the invention is directed to providing a fiber-optic surface plasmon resonance sensor sensitively operating in the visible, near infrared to mid-infrared region, which has a surface plasmon excitation layer with an optical waveguide layer inserted between two excitation layers, wherein the control of the surface plasmon resonance wavelength is easily achievable in a broad range via the adjustment of the thickness of the optical waveguide layer and signal stabilization is possible through self-calibration using s-polarized optical waveguide mode as a self-referencing channel, and a sensing method using the same.

A fiber-optic surface plasmon resonance sensor according to an exemplary embodiment may include an optical fiber and a surface plasmon excitation layer. The optical fiber may include a core, a cladding surrounding the core, and a depression. The surface plasmon excitation layer may include a first excitation layer, a second excitation layer and an optical waveguide layer between the first excitation layer and the second excitation layer.

A sensing method according to an exemplary embodiment may include: entering incident light through a core of an optical fiber including the core, a cladding surrounding the core, and a depression; coupling the incident light into a surface plasmon excitation layer provided on the depression and including a first excitation layer, a second excitation layer and an optical waveguide layer between the first excitation layer and the second excitation layer; and detecting an analyte in contact with the surface plasmon excitation layer by measuring light exit from the optical fiber.

The fiber-optic surface plasmon resonance sensor and the sensing method according to the embodiments of the invention may provide excellent tunability of surface plasmon resonance wavelength through control of the thickness of the optical waveguide layer of the surface plasmon excitation layer. Furthermore, self-calibration is possible using the waveguide mode generated in the optical waveguide layer due to the s-polarized light, and multiple surface plasmon resonance modes may be generated by increasing the thickness of the optical waveguide layer and the modes may be used selectively. In addition, since the surface plasmon resonance condition can be fine-tuned over a broad range, the sensitivity of the fiber-optic sensor can be remarkably improved and a fiber-optic surface plasmon resonance sensor operable in the near infrared to mid-infrared region where the superior sensitivity to the change in external environment, local electric field penetration depth and molecular selectivity can be provided.

BRIEF DESCRIPTION OF THE DRAWINGS

The above and other objects, features and advantages of the present disclosure will become apparent from the following description of certain exemplary embodiments given in conjunction with the accompanying drawings, in which.

DETAILED DESCRIPTION OF EMBODIMENTS

Hereinafter, exemplary embodiments will be described in detail with reference to the accompanying drawings.

Figure 1:
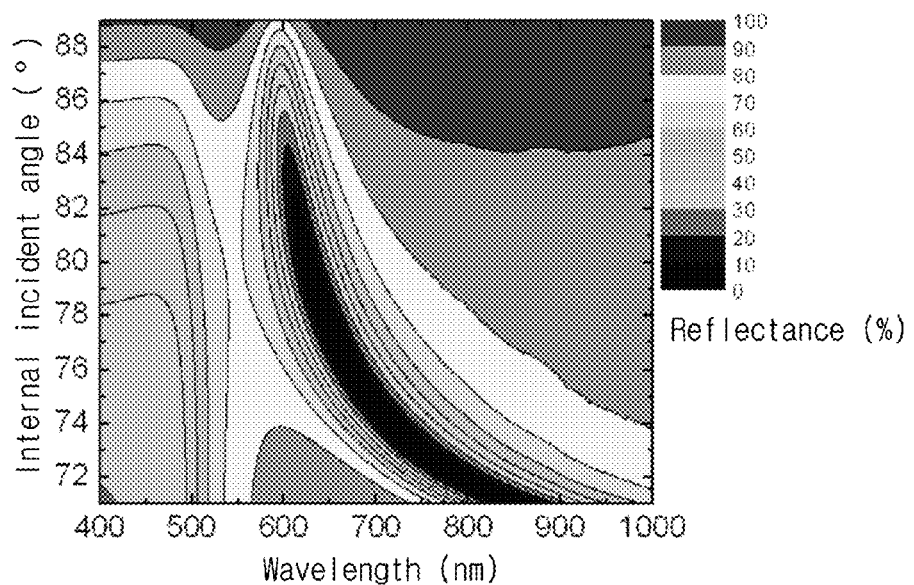
FIG. 1 is a contour map showing a theoretical calculation result of internal reflectance of a conventional fiber-optic surface plasmon resonance sensor as a function of internal incident angle and wavelength of incident light.
Figure 2:
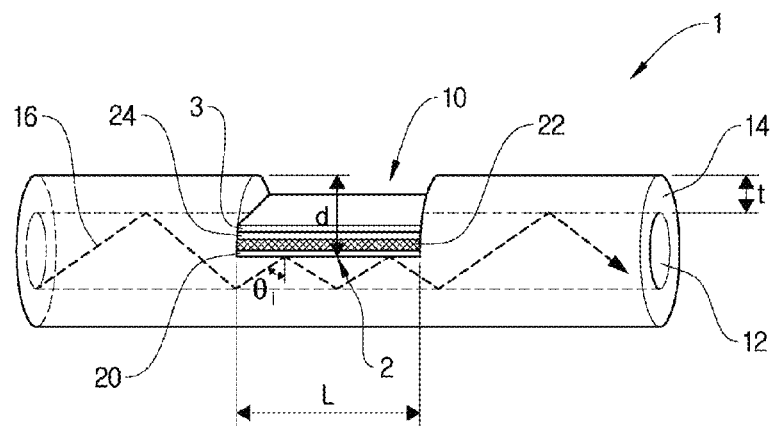
FIG. 2 schematically shows the configuration of a fiber-optic surface plasmon resonance sensor according to an exemplary embodiment.

FIG. 2 schematically shows the configuration of a fiber-optic surface plasmon resonance sensor according to an exemplary embodiment.

Referring to FIG. 2, a fiber-optic surface plasmon resonance sensor according to an exemplary embodiment may include an optical fiber 1 and a surface plasmon excitation layer 2. The optical fiber 1 may include a core 12, a cladding 14 and a depression 10. The core 12 and the cladding 14 may extend along one direction, and the cladding 14 may be disposed to surround the core 12. The core 12 may include any material which is optically transparent at an operation wavelength. The cladding 14 may include any material whose refractive index is lower than the refractive index of the core 12.

The depression 10 may be formed on a side surface of the optical fiber 1, i.e. in a direction perpendicular to the length direction of the optical fiber 1. The depression 10 may be formed by polishing the side surface of the optical fiber 1. In an exemplary embodiment, the depth d of the depression 10 may be equal to or larger than the thickness t of the cladding 14. When the depth d of the depression 10 is exactly the same as the thickness t of the cladding 14, the cladding 14 will be completely removed in at least a portion of the bottom of the depression 10 and the core 12 will be exposed. And, when the depth d of the depression 10 is larger than the thickness t of the cladding 14, the core 12 may be exposed such that a portion of the core 12 is concave.

The surface plasmon excitation layer 2 may be provided on the depression 10. As a consequence, the surface plasmon excitation layer 2 is in contact with the core 12 exposed by the depression 10. The surface plasmon excitation layer 2 may include a first excitation layer 20, an optical waveguide layer 22 and a second excitation layer 24. The first excitation layer 20 may be provided on the exposed portion of the core 12, and the optical waveguide layer 22 may be provided on the first excitation layer 20. And, the second excitation layer 24 may be provided on the optical waveguide layer 22. For example, after polishing a side surface of the optical fiber 1 so that the core 12 is exposed, the first excitation layer 20, the optical waveguide layer 22 and the second excitation layer 24 may be sequentially formed on the exposed portion of the core 12.

The optical waveguide layer 22 may include any material which is optically transparent at an operation wavelength, i.e. the wavelength of incident light 16. And, the first excitation layer 20 and the second excitation layer 24 may include any material whose optical property at the operation wavelength can be explained by the Drude metal model. For example, the first excitation layer 20 and the second excitation layer 24 may include a noble metal such as gold (Au), silver (Ag) and copper (Cu), a transition metal, an alloy thereof, or any other suitable metal material. Alternatively, the first excitation layer 20 and the second excitation layer 24 may include a semiconductor material, a transparent conducting oxide, a carbon material such as graphene, a chalcogenide material, or the like. These materials may be advantageous in the application of the fiber-optic surface plasmon resonance sensor in the infrared region since their optical behavior in the infrared region is determined by the Drude metal model.

In an exemplary embodiment, the first excitation layer 20 may include a dielectric material whose refractive index is lower than the refractive indices of the core 12 and the optical waveguide layer 22. For example, the first excitation layer 20 may include $MgF_2$, Teflon or any other suitable dielectric material, without being limited thereto.

The incident light 16 incident from one end of the optical fiber 1 to the core 12 is propagated as confined within the core 12. The incident light 16 is totally reflected with an angle of incidence $\theta_i$ with respect to the surface plasmon excitation layer 2. The number of total reflections of the incident light 16 at the surface plasmon excitation layer 2 depends at least in part on the angle of incidence $\theta_i$ of the incident light 16 with respect to the surface plasmon excitation layer 2, the length L of the surface plasmon excitation layer 2, the distance from the surface plasmon excitation layer 2 to the interface between the core 12 and the cladding 14, i.e. the distance from the bottom surface of the first excitation layer 20 to the interface between the core 12 and the cladding 14, and so forth.

At the specific angle of incidence $\theta_i$ and wavelength that satisfy the surface plasmon resonance condition, the incident light 16 propagating through the core 12 is coupled to the surface plasmon excitation layer 2 and excites a surface plasmon wave. As a result, at the corresponding angle of incidence $\theta_i$ and wavelength, significant decrease in the intensity of light exit from the optical fiber 1 after passing through the core 12 or being reflected at a specific location, i.e. an intensity dip occurs. The dip depth of the exit light increases in proportion to the number of total reflections of the incident light 16 at the surface plasmon excitation layer 2. Since the surface plasmon resonance condition depends very sensitively on the change in the environment surrounding the surface plasmon excitation layer 2, an analyte in contact with the surface plasmon excitation layer 2 can be detected by analyzing the dip of the exit light.

The detection of the signal of the fiber-optic surface plasmon resonance sensor may be achieved by monitoring the location of the intensity dip in the transmittance or reflectance spectrum caused by a light absorption due to the surface plasmon resonance, or by monitoring the change in the intensity of the transmitted or reflected light at specific wavelength. For example, the incident light 16 for spectroscopic analysis may be white light. Also, the sensor operation detecting the relative change in signal intensity at the resonance wavelength owing to the change in external environment is possible with monochromatic light. However, the incident light 16 is not limited to white light or monochromatic light, and it may be polychromatic light.

The incident light may include a p-polarized component (or p-wave) whose electric field is parallel to the plane of incidence and/or an s-polarized component (or s-wave) whose electric field is perpendicular thereto depending on the polarization direction. The p-polarized light component and the s-polarized light component exhibits quite different sensitivity to the analyte in contact with the surface plasmon excitation layer 2. The intensity dip in the exit light corresponding to the p-polarized component of the incident light is very sensitive to the change in the optical property of the analyte, while the dip corresponding to the s-polarized component is relatively insensitive to the change of the analyte. Since both the p-polarized component and the s-polarized component are affected by the system noise, self-calibration of removing the noise from the pure signal is possible by utilizing the difference in sensitivity of the p-polarized component and the s-polarized component. This will be described in detail later.

In the embodiment illustrated in FIG. 2, the surface plasmon excitation layer 2 is disposed on the bottom of the depression 10 such that it is directly in contact with the core 12 of the optical fiber 1. However, in another exemplary embodiment, a buffer layer (not shown) may be provided between the optical fiber 1 and the surface plasmon excitation layer 2. The buffer layer may include, for example, a dielectric material. The buffer layer may improve flatness at the interface or may serve as a diffusion barrier. In another exemplary embodiment, an interface adhesion layer (not shown) may be provided between the optical fiber 1 and the surface plasmon excitation layer 2. The interface adhesion layer is a layer for improving adhesion between the optical fiber 1 and the plasmon excitation layer 2. The interface adhesion layer may include, for example, Ti, W, Cr, TiN, $Ta_2O_5$, TCO, ZnS—$SiO_2$ or other suitable material.

In another exemplary embodiment, the fiber-optic surface plasmon resonance sensor may further include a sensing layer 3 provided on the second excitation layer 24 of the surface plasmon excitation layer 2 and having a refractive index changing in response to the change in external environment. The sensing layer may include a material whose optical property changes sensitively in response to the external environment such as chemical gas, liquid, etc. A variety of materials including, for example, metal oxides, organic polymer materials, chalcogenide materials, semiconductor materials, etc., may be used for the sensing layer without limitation.

Figure 3:
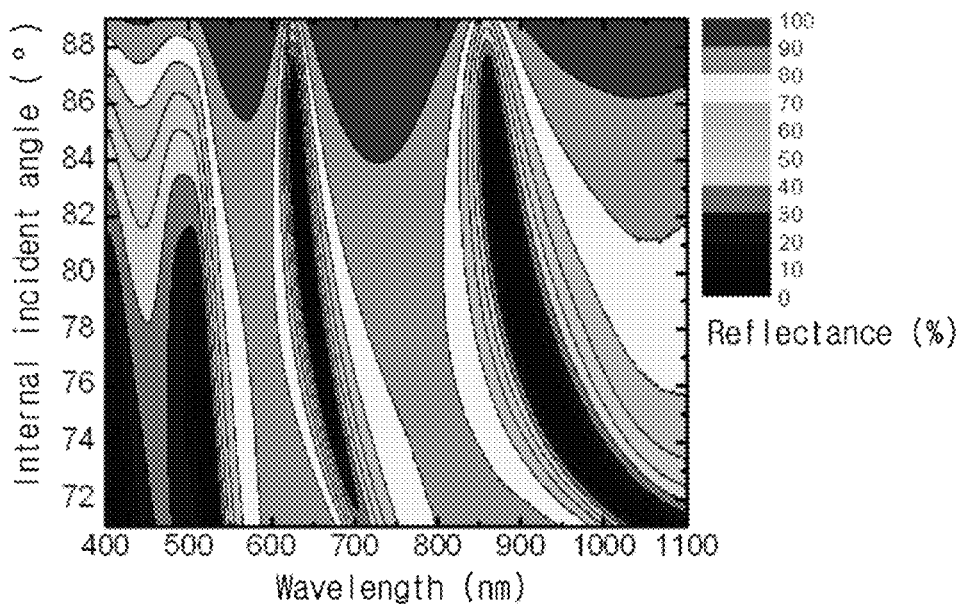
FIGS. 3 and 4 are contour maps showing theoretical calculation results of internal reflectance of a fiber-optic surface plasmon resonance sensor according to an exemplary embodiment as a function of internal incident angle and wavelength of incident light.

FIG. 3 is a contour map showing a theoretical calculation result of internal reflectance inside a core of a fiber-optic surface plasmon resonance sensor according to an exemplary embodiment as a function of internal incident angle and wavelength of incident light. FIG. 3 shows a 2-dimensional contour map calculated for a fiber-optic surface plasmon resonance sensor wherein the optical fiber core includes $SiO_2$, first and second excitation layers of a surface plasmon excitation layer include 18-nm thick gold (Au), and an optical waveguide layer includes 400-nm thick ZnS—$SiO_2$. It is assumed that the medium surrounding the surface plasmon excitation layer is water and the incident light is p-polarized. Unlike the conventional fiber-optic surface plasmon resonance sensor, multiple reflectance dips are observed as a result of surface plasmon resonance near about 650 nm and about 900 nm.

Figure 4:
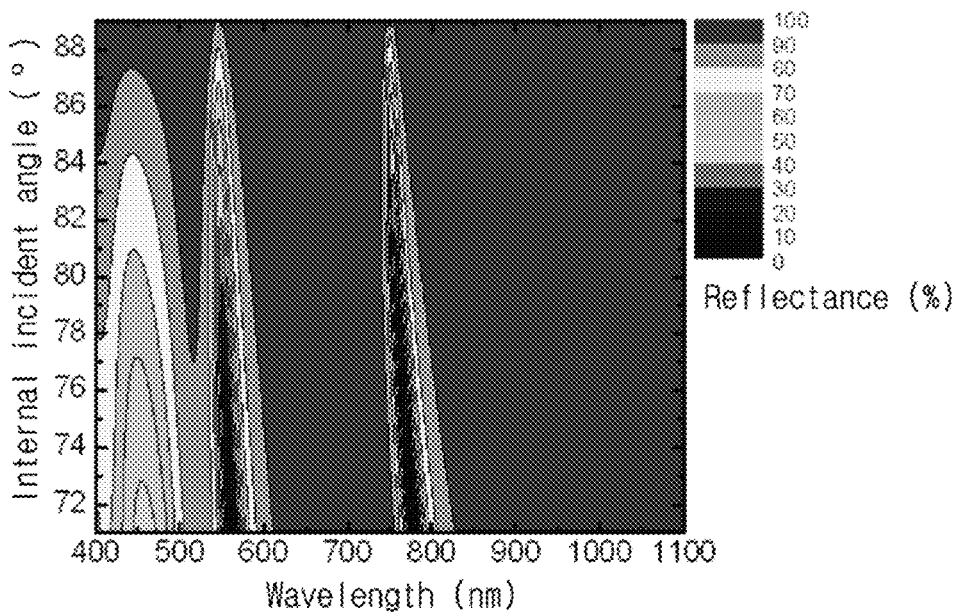

FIG. 4 is a contour map showing another theoretical calculation result of reflectance in a fiber-optic surface plasmon resonance sensor according to an exemplary embodiment as a function of internal incident angle and wavelength of incident light. FIG. 4 shows a result for s-polarized incident light for the same case as shown in FIG. 3. As shown in the figure, very sharp multiple reflectance dips are observed unlike the conventional fiber-optic surface plasmon resonance sensor. These sharp reflectance dips occur because the surface plasmon excitation layer has the optical waveguide layer between the first excitation layer and the second excitation layer. Specifically, they occur because the s-polarized incident light propagating in the core is coupled to the guided wave mode in the optical waveguide layer under specific phase matching condition.

Figure 5:
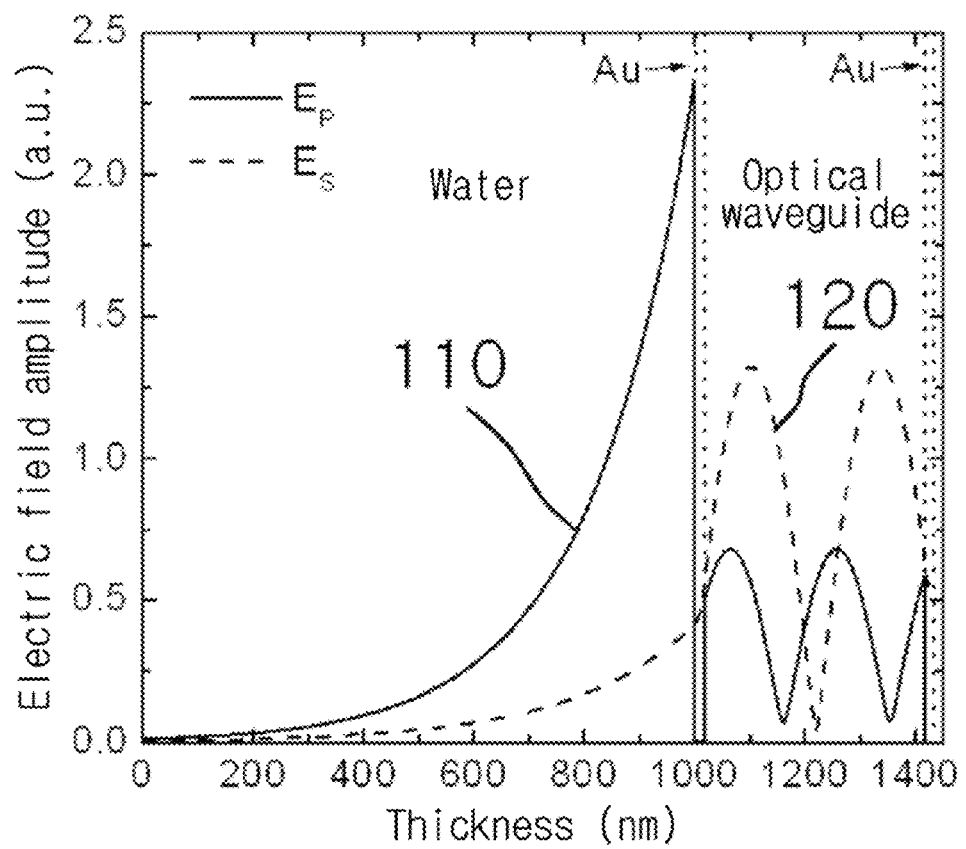
FIG. 5 is a graph showing a distribution of the electric field amplitude at the reflectance dips shown in FIGS. 3 and 4 along a thickness direction of a multilayer stack structure.

FIG. 5 is a graph showing an amplitude distribution of the electric field at the reflectance dips shown in FIGS. 3 and 4 along a thickness direction of a multilayer stack. The two graphs 110, 120 in FIG. 5 show calculation results of distribution of the electric field amplitude $E_p$, $E_s$ for p- and s-polarized incident light, respectively. The graph 110 shows a calculation result of the amplitude distribution of electric field of the p-polarized incident light at the dip of 640 nm and an internal incident angle of 81°. The graph 120 shows a calculation result of the amplitude distribution of electric field of the s-polarized incident light at the dip of 757 nm and an internal incident angle of 81°.

Referring to the graph 110, the electric field at the reflectance dip due to the p-polarized incident light exhibit the typical surface plasmon resonance characteristics where the electric field is concentrated at the outer surface of the second excitation layer such that the intensity of the electric field is strongest at the surface and decays exponentially toward the external medium. In contrast, referring to the graph 120, the electric field at the reflectance dip due to the s-polarized incident light exhibits the typical optical waveguide mode characteristics with most of energy confined within the optical waveguide layer of the surface plasmon excitation layer and only a portion of the electric field leaking to the external medium.

The significant difference in the electric field distribution occurring at the interface with the external medium leads to the significant difference in sensitivity between the p-wave mode and the s-wave mode in response to the change in external environment. The surface plasmon resonance mode by p-wave is very sensitive to the change in the optical property of the external medium in contact with the surface plasmon excitation layer, whereas the optical waveguide mode by s-wave is relatively insensitive to the change in the external medium.

Accordingly, utilizing the s-polarized light component, the change in the signal caused by the analyte exist on the surface of the surface plasmon excitation layer may be corrected by excluding the external system noise factors such as fluctuation in the light source, temperature increase of the measurement system, or the like. That is to say, by comparing the reflectance of the p-polarized light component with that of the s-polarized component, the external system noise component reflected in the s-polarized light signal may be removed from the p-polarized light signal and only the pure signal change from the analyte can be detected.

Figure 6:
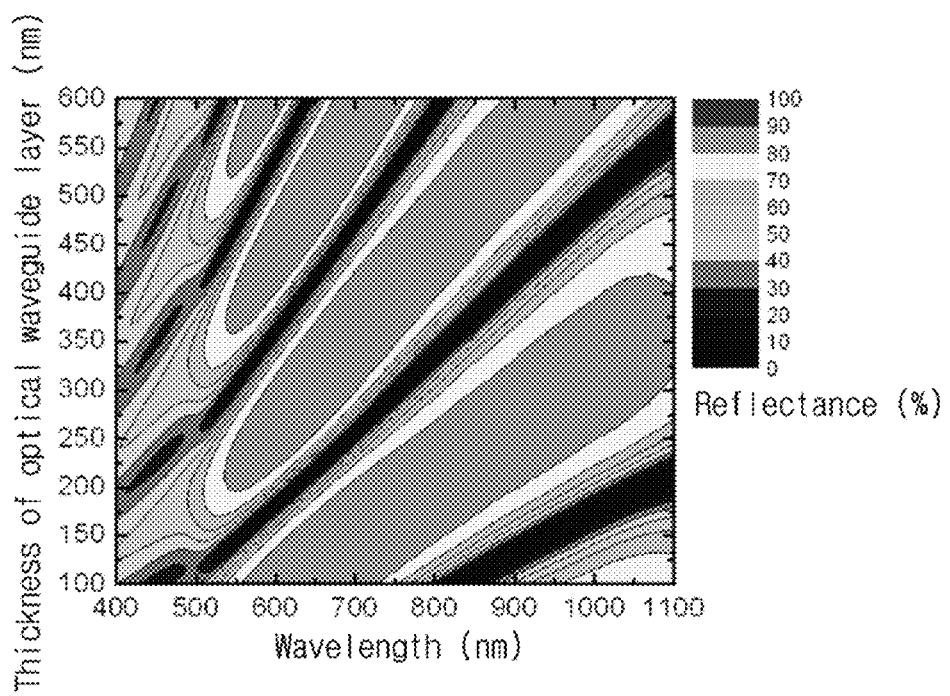
FIG. 6 is a contour map showing a theoretical calculation result of reflectance of a p-polarized light component of a fiber-optic surface plasmon resonance sensor according to an exemplary embodiment as a function of the thickness of an optical waveguide layer and wavelength of incident light.

FIG. 6 is a contour map showing a theoretical calculation result of reflectance of a p-polarized light component for a fiber-optic surface plasmon resonance sensor according to an exemplary embodiment as a function of thickness of an optical waveguide layer and wavelength of incident light. The angle of incidence of the incident light is fixed at 81°. It can be seen that the number of surface plasmon resonance modes increases with the thickness of the optical waveguide layer. It may be because, as described with respect to the distribution of the electric field amplitude referring to FIG. 5, the coupling between the plasmonic mode owing to the first and second excitation layers of the surface plasmon excitation layer and the optical waveguide mode owing to the optical waveguide layer occurs in multiple numbers with periodicity dependent on the thickness of the optical waveguide layer.

Figure 7:
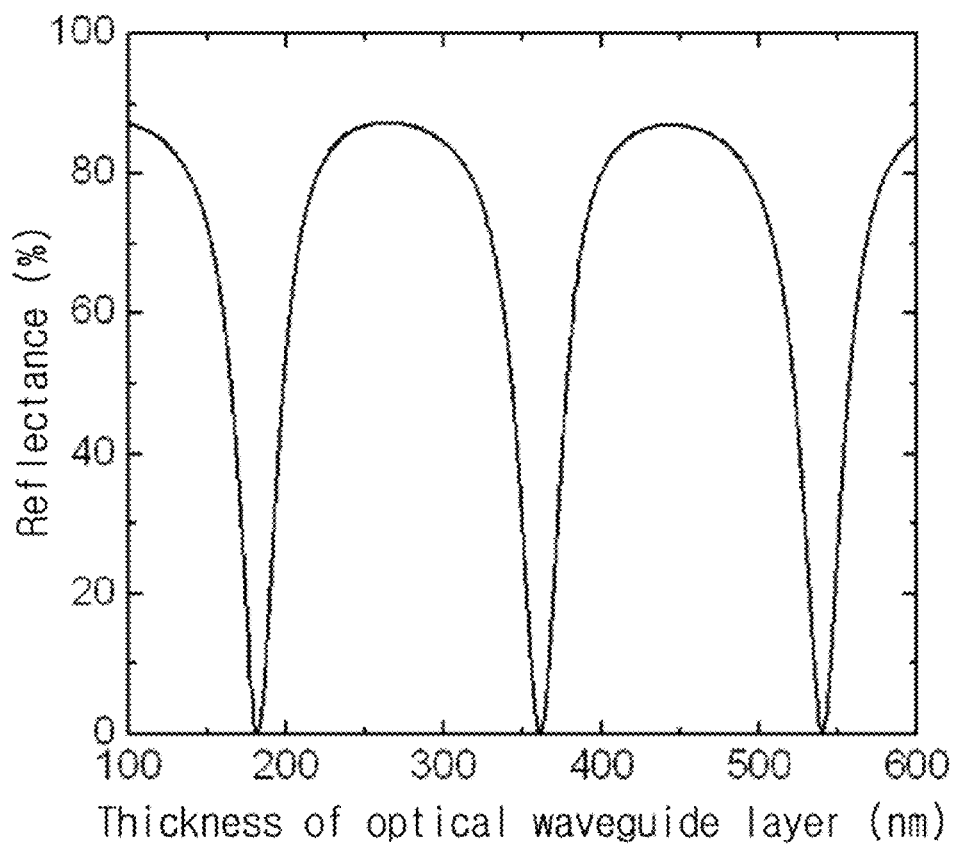
FIG. 7 is a graph showing reflectance at a wavelength of 600 nm taken from the contour map of FIG. 6 as a function of the thickness of the optical waveguide layer.

FIG. 7 is a graph showing reflectance at a wavelength of 600 nm in the contour map of FIG. 6 as a function of the thickness of the optical waveguide layer. As seen from the figure, dips occur periodically with thickness intervals of about 179 nm at the given conditions. Also, as seen from the contour map of FIG. 6, the periodic intervals of the optical waveguide layer thickness where the plasmonic resonance dip occurs increase with the wavelength of the incident light.

Figure 8:
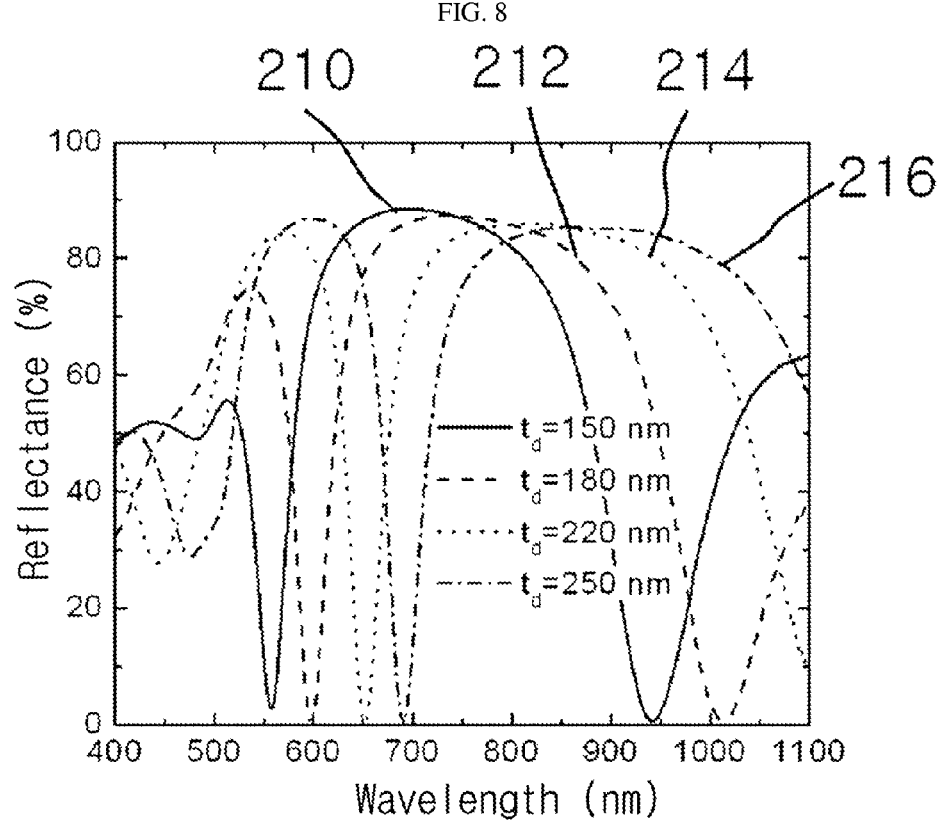
FIG. 8 is a graph showing reflectance curves taken from the contour map of FIG. 6 when the thickness of the optical waveguide layer is 150 nm, 180 nm, 220 nm and 250 nm, respectively, as a function of wavelength.

FIG. 8 is a graph showing reflectance curves in the contour map of FIG. 6 when the thickness of the optical waveguide layer $t_d$ is 150 nm, 180 nm, 220 nm and 250 nm, respectively, as a function of wavelength. The four graphs 210, 212, 214, 216 are reflectance curves when the thickness of the optical waveguide layer $t_d$ is 150 nm, 180 nm, 220 nm and 250 nm, respectively. It is assumed that both the first excitation layer and the second excitation layer include 18-nm thick gold. As seen from the figure, with the thickness of the first excitation layer and the second excitation layer fixed, the surface plasmon resonance wavelength can be easily controlled in a very broad range only by varying the thickness of the optical waveguide layer. It can also be seen that the resonance wavelength red-shifts as the thickness of the optical waveguide layer increases, and the degree of red-shift is larger in the long-wavelength mode.

This tunability of resonance wavelength provides advantages to the fiber-optic surface plasmon resonance sensor in various aspects. For example, since a surface plasmon resonance sensor using a single-mode optical fiber uses monochromatic light, it can operate based only on intensity interrogation. For the sensor to operate, the surface plasmon resonance condition should be satisfied within the refractive index range of the medium to be measured. And, to improve signal linearity and sensitivity, it is favorable that measurement be made slightly away from the resonance dip. However, since the light source is the only control parameter to satisfy these requirements in the prior art, a light source allowing for wavelength fine-tuning in a broad range is needed, which renders the device impractical. In contrast, since the optical fiber surface plasmon sensor according to embodiments has excellent wavelength tunability only via the control of the thickness of the optical waveguide layer, a sensor with optimal signal sensitivity can be realized with a light source of any wavelength.

When a multi-mode optical fiber is used in the optical fiber surface plasmon sensor according to the embodiments, operation based on wavelength interrogation is possible and the operation wavelength can be arbitrarily selected without limitation. Some analyte requires a sensor that operates in the near infrared to mid-infrared region, where the fundamental vibration modes of most molecules exist, as well as the visible region. In the infrared region, the decay length of the local electric field increases and it is possible to measure an analyte relatively farther from the sensor surface. Also, the sensor sensitivity is improved significantly through interaction with the molecular vibration mode and the spectroscopic analysis based on energy transfer is possible. In the prior art, the surface plasmon resonance wavelength is restricted to a very narrow range without regard to the use of the multi-mode optical fiber. In contrast, the optical fiber surface plasmon sensor according to the embodiments is without such restriction.

Figure 9:
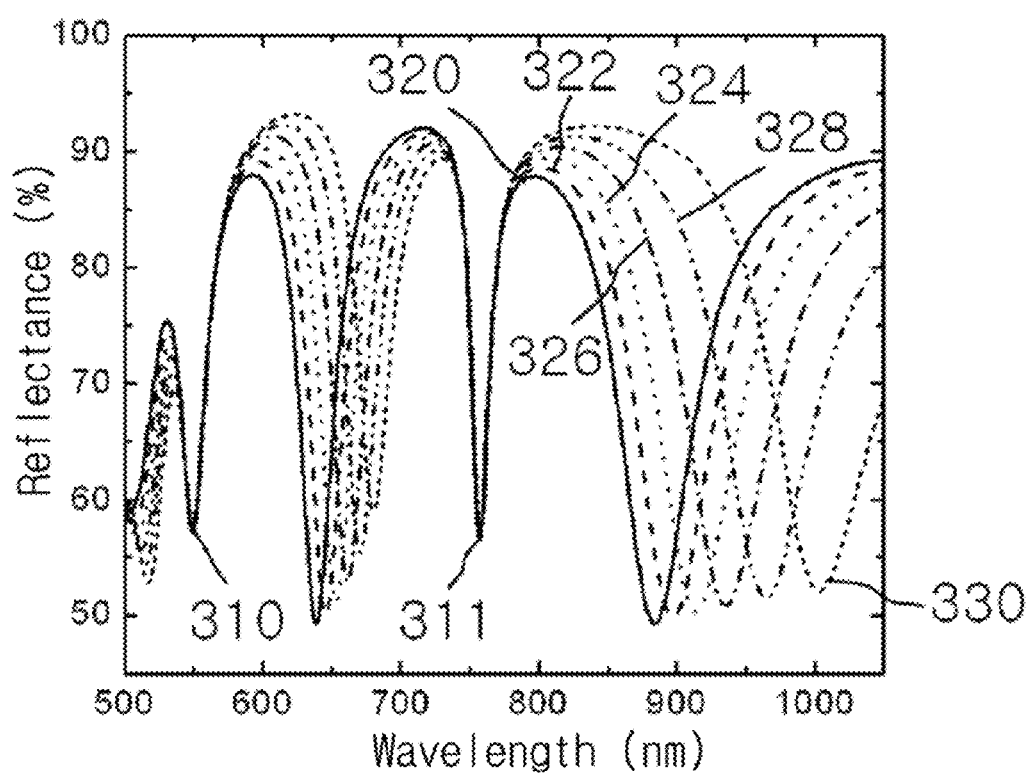
FIG. 9 is a graph showing reflectance curves of a fiber-optic surface plasmon resonance sensor according to an exemplary embodiment in response to change in the bulk refractive index of surrounding medium as a function of wavelength.

FIG. 9 is a graph showing reflectance curves of a fiber-optic surface plasmon resonance sensor according to an exemplary embodiment in response to change in the bulk refractive index of surrounding medium as a function of wavelength. FIG. 9 shows change in reflectance curve with the change in the refractive index of surrounding medium for a stack structure in which a first excitation layer and a second excitation layer each include 18-nm thick gold (Au) and an optical waveguide layer including 400-nm thick ZnS—SiO$_2$ is inserted between the first excitation layer and the second excitation layer, when random polarized light having p- and s-polarized components mixed is incident and propagated through a silica core.

The 6 graphs 320, 322, 324, 326, 328, 330 in FIG. 9 are reflectance curves when the refractive index of the surrounding medium is changed from 1.33 (water) to 1.34, 1.35, 1.36, 1.37 and 1.38, respectively. The dips occurring around 640 nm and 887 nm correspond to the surface plasmon resonance mode by the p-polarized component of the incident light. And, the dips occurring around 550 nm and 757 nm in the two graphs 310, 311 correspond to the optical waveguide mode by the s-polarized component of the incident light.

As seen from the figure, the two modes are significantly different in sensitivity to the change in the refractive index of the external medium. The surface plasmon resonance mode by the p-polarized component responds very sensitively to the change in the refractive index of the external medium and the resonance wavelength is shifted to longer wavelength as the refractive index of the external medium increases. In contrast, the optical waveguide mode due to the s-polarized component is relatively insensitive and exhibits little change. The sensitivity defined by the change in dip wavelength per unit refractive index change is one, two or more order of magnitude lower for the s-wave mode as compared to the p-wave mode. However, the s-wave mode is affected by the system noise such as fluctuation of the light source intensity, variation in the optical constants of the materials constituting the sensor due to the temperature change of the surrounding environment, or the like, like the p-wave mode. Accordingly, self-referencing of compensating for the system noise from the surface plasmon resonance signal is possible using the s-wave mode without an additional reference channel.

The difference in sensitivity of the multiple modes of surface plasmon resonance with wavelength is also noticeable. From the comparison of the graphs 320, 322, 324, 326, 328, 330 in FIG. 9, the sensitivity of the change in dip wavelength with respect to the change in the refractive index of the external medium can be calculated. Among the surface plasmon resonance modes, the dip near 640 nm has a sensitivity of about 828 nm/RIU (refractive index unit), whereas the dip at relatively longer wavelength of about 887 nm wavelength has a significantly improved sensitivity of about 2017 nm/RIU. Therefore, improved sensitivity can be achieved in the longer-wavelength, near infrared to mid-infrared region. Although the infrared region is important since most of molecular vibration modes exist in the frequency region, it was practically impossible to realize a fiber-optic surface plasmon resonance sensor that operates in the near infrared to mid-infrared region using the prior art. In contrast, the optical fiber surface plasmon sensor according to the embodiments is remarkably advantageous since it is operable in the near infrared to mid-infrared region.

In an exemplary embodiment, the material of the optical fiber and the surface plasmon excitation layer may be selected adequately for operation in the infrared region. For example, the core of the optical fiber may include sapphire, silicon, germanium, ZnSe, chalcogenide or other suitable material having superior light transmittance in the infrared region. And, the first and second excitation layers of the surface plasmon excitation layer may include a noble metal such as Au or Ag, a transition metal, a semiconductor material, a transparent conducting oxide, a carbon material such as graphene, a chalcogenide material or other suitable material whose optical behavior in the infrared region can be described by the Drude metal model without limitation.

In actual applications to a sensing system, the incident light may be either linearly polarized or randomly polarized. When the incident light is randomly polarized, the resonance wavelength of the surface plasmon mode by the p-polarized component of the incident light may be prevented from being superimposed with the wavelength of the optical waveguide mode due to the s-polarized component to avoid affecting the signal detection.

At least one of the position of the surface plasmon resonance mode wavelengths by the p-polarized light component, the separation between the surface plasmon resonance mode wavelengths, and the separation between the surface plasmon resonance mode wavelengths and the optical waveguide mode wavelength due to the s-polarized component may be adjusted by controlling, in addition to the thickness of the optical waveguide layer, the material of the first excitation layer and the second excitation layer of the surface plasmon excitation layer, the thickness of the first excitation layer and the second excitation layer, and/or the thickness ratio of the first excitation layer and the second excitation layer. For example, by decreasing the thickness of the second excitation layer which is the outer layer, the separation between the surface plasmon resonance wavelength in the shorter-wavelength region and the surface plasmon resonance wavelength in the longer-wavelength region can be increased. Especially, red-shift of the longer-wavelength mode becomes prominent. Meanwhile, the position of the resonance wavelength of the optical waveguide mode due to the s-polarized component is hardly affected.

Figure 10:
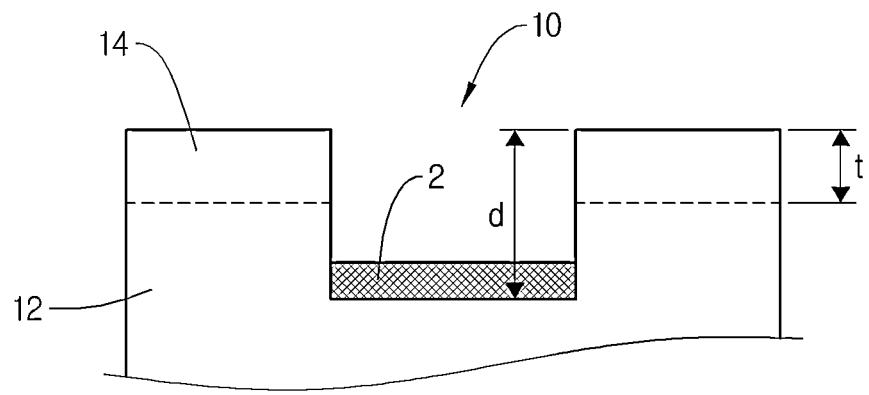
FIGS. 10 and 11 are longitudinal cross-sectional views illustrating the position of a surface plasmon excitation layer in a fiber-optic surface plasmon resonance sensor according to an exemplary embodiment.

FIG. 10 is a longitudinal cross-sectional view showing the position of the surface plasmon excitation layer in a fiber-optic surface plasmon resonance sensor according to an exemplary embodiment. In FIG. 10, the core 12 is partly polished such that the depth d of the depression 10 is larger than the thickness t of the cladding 14. The surface plasmon excitation layer 2 may be provided on the polished surface of the core 12 formed on the depression 10.

Figure 11:
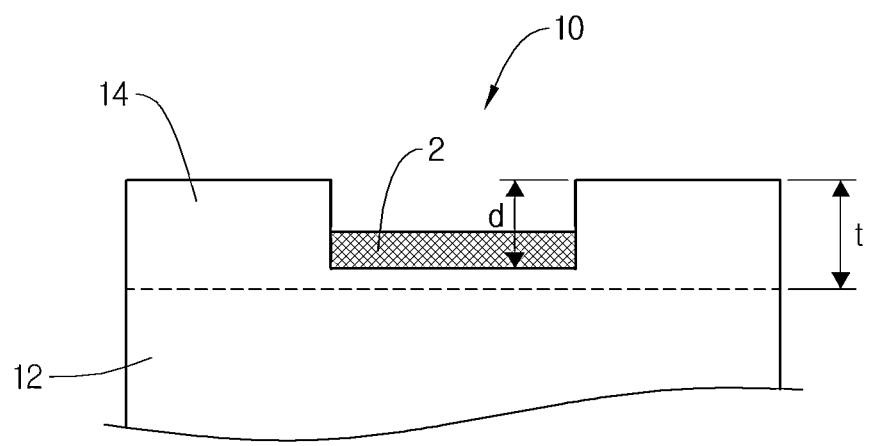

FIG. 11 is a longitudinal cross-sectional view showing the position of the surface plasmon excitation layer in a fiber-optic surface plasmon resonance sensor according to another exemplary embodiment. In FIG. 11, the optical fiber is polished such that the depth d of the depression 10 is smaller than the thickness t of the cladding 14. As a consequence, the cladding 14 is not completely removed but remains thin, and the surface plasmon excitation layer 2 is provided on the polished cladding 14. The thickness of the thin cladding 14 between the core 12 and the surface plasmon excitation layer 2 may be smaller than the mode diameter of the light propagating through the core 12. The mode diameter refers to the effective range of the electric field of the propagation mode confined in the core 12. As a result, the incident light propagating through the core 12 may be coupled into the surface plasmon excitation layer 2 at the angle of incidence and wavelength satisfying the surface plasmon resonance condition. In the embodiment shown in FIG. 11, error caused by distortion of the incident light propagating through the core 12 due to physical discontinuity can be decreased and/or prevented and a more stable signal can be acquired since the core 12 is not polished.

Figure 12:
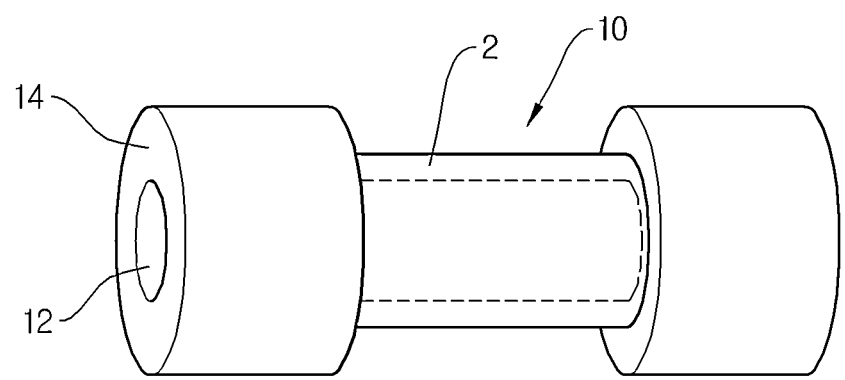
FIG. 12 schematically shows the configuration of a fiber-optic surface plasmon resonance sensor according to another exemplary embodiment.

FIG. 12 schematically shows the configuration of a fiber-optic surface plasmon resonance sensor according to another exemplary embodiment.

Referring to FIG. 12, instead of polishing only one side of the optical fiber, an annular-shaped depression 10 may be formed at a specific portion of the optical fiber. It may be achieved by removing the circumference of the optical fiber by a chemical and/or physical method. Also, an annular-shaped surface plasmon excitation layer 2 may be formed on the depression 10. When compared with the case where the depression is formed by polishing only one side of the optical fiber, a deeper resonance dip signal can be obtained and the signal-to-noise ratio can be maximized since the surface plasmon resonance condition for the p-wave is satisfied in all directions at the cross section of the core 12.

Figure 13:
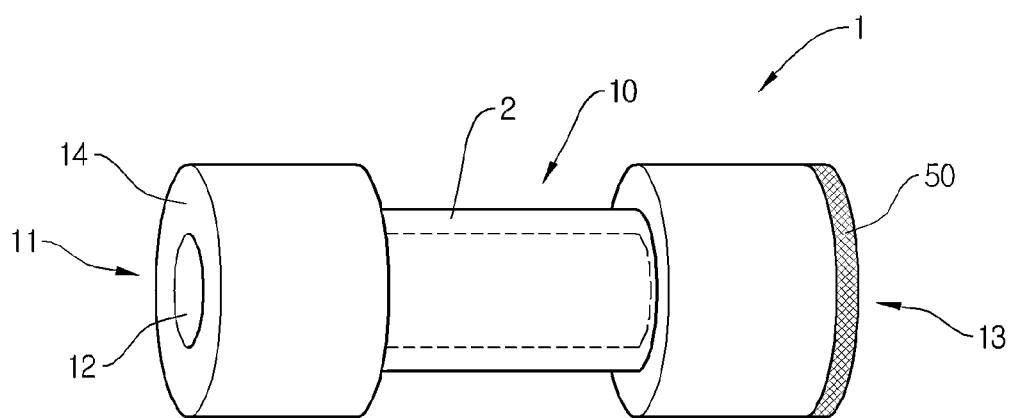
FIG. 13 schematically shows the configuration of a fiber-optic surface plasmon resonance sensor according to still another exemplary embodiment.

FIG. 13 schematically shows the configuration of a fiber-optic surface plasmon resonance sensor according to another exemplary embodiment. FIG. 13 shows a reflection type fiber-optic surface plasmon resonance sensor having a reflective layer 50. When the fiber-optic surface plasmon resonance sensor is configured as a transmission type sensor, the fiber-optic surface plasmon resonance sensor may be disposed serially between the light source and the optical detector. In contrast, the reflection type sensor may be configured such that the light source and the optical detector are in the same direction with respect to the optical fiber using a 2×1 splitter, a bifurcated optical fiber assembly, or the like.

In order to enable the configuration of the reflection type sensor, the fiber-optic surface plasmon resonance sensor according to an exemplary embodiment may include the reflective layer 50. For example, the reflective layer 50 may be a mirror. The optical fiber 1 may include a first end 11 at which the incident light is incident through the core 12, and a second end 13 opposite to the first end 11. The depression 10 of the optical fiber corresponding to the sensing region may be provided between the first end 11 and the second end 13. The incident light incident from the first end 11 may be reflected at the reflective layer 50 after passing the surface plasmon excitation layer 2 and then be exit again through the first end 11. The medium surrounding the surface plasmon excitation layer 2 may be detected by measuring the light exit from the optical fiber 1.

When the fiber-optic surface plasmon resonance sensor is configured as reflection type as described above, system configuration is easier as compared to the transmission type which has difficulty in disposing the optical detector. Also, only the sensor probe may be inserted or put in a specific portion of the sample to be detected. In addition, the dip signal is enhanced since the light reflected at the reflective layer 50 passes the surface plasmon excitation layer 2 once more.

Figure 14:
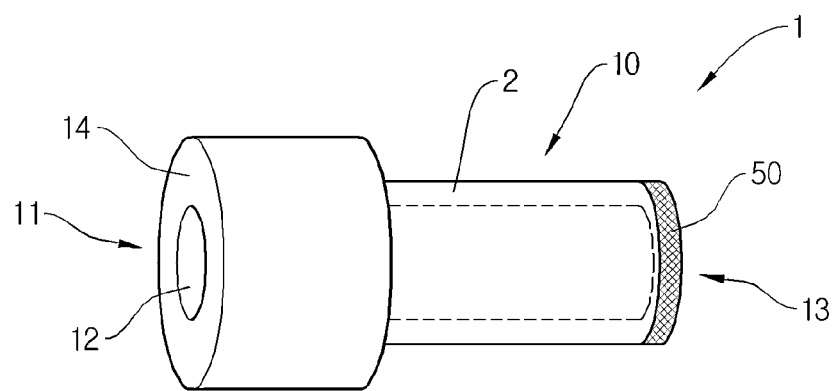
FIG. 14 schematically shows the configuration of a fiber-optic surface plasmon resonance sensor according to still another exemplary embodiment.

FIG. 14 schematically shows the configuration of a fiber-optic surface plasmon resonance sensor where the position of the reflective layer is different from that of the fiber-optic surface plasmon resonance sensor of FIG. 13. Whereas the reflective layer 50 is spaced apart from the surface plasmon excitation layer 2 along the length direction of the optical fiber 1 in the embodiment illustrated in FIG. 13, the reflective layer 50 is formed directly at the end of the core 12 in contact with the surface plasmon excitation layer 2 in the embodiment illustrated in FIG. 14.

FIGS. 13 and 14 show the embodiments where the reflective layer 50 is provided in the fiber-optic surface plasmon resonance sensor with the depression 10 formed in an annular shape along the periphery of the optical fiber 1. However, this is only exemplary and the reflective layer 50 may be identically provided in the fiber-optic sensor with the depression 10 formed by polishing the side of the optical fiber 1 described referring to FIG. 2.

The fiber-optic surface plasmon resonance sensor and the sensing method using the same described above may provide excellent tunability of surface plasmon resonance wavelength through control of the thickness of the optical waveguide layer in the surface plasmon excitation layer. Furthermore, self-calibration is possible using the waveguide mode formed by the s-polarized light component, and multiple surface plasmon resonance modes may be generated by increasing the thickness of the optical waveguide layer for selective use. In addition, since the surface plasmon resonance condition can be fine-tuned over a broad range, the sensitivity of the fiber-optic sensor can be remarkably improved and a fiber-optic surface plasmon resonance sensor operable in the near infrared to mid-infrared region where the superior sensitivity to the change in external environment, local electric field penetration depth and molecular selectivity can be provided. The fiber-optic surface plasmon resonance sensor according to an embodiment may also be applied to an integrated optical waveguide sensor. In this case, it may provide advantages in the configuration of a multi-channel sensor array chip for multiplexed analysis.

While the present disclosure has been described with respect to the specific embodiments, it will be apparent to those skilled in the art that various changes and modifications may be made without departing from the spirit and scope of the disclosure as defined in the following claims.

What is claimed is:

1. A fiber-optic surface plasmon resonance sensor comprising:
   an optical fiber comprising a core, a cladding surrounding the core, and a depression; and
   a surface plasmon excitation layer provided on the depression,
   wherein the surface plasmon excitation layer comprises a first excitation layer, a second excitation layer and an optical waveguide layer between the first excitation layer and the second excitation layer, the optical waveguide layer being a single layer, and
   wherein the surface plasmon excitation layer is configured such that incident light propagating through the core and satisfying a surface plasmon resonance condition is coupled into the optical waveguide layer in optical waveguide mode and such that a surface plasmon wave is excited in the surface plasmon excitation layer by the incident light coupled into the optical waveguide layer.

2. The fiber-optic surface plasmon resonance sensor according to claim 1, wherein the depth of the depression is equal to or larger than the thickness of the cladding, and the surface plasmon excitation layer is in contact with the core through the depression.

3. The fiber-optic surface plasmon resonance sensor according to claim 1, wherein the depth of the depression is smaller than the thickness of the cladding, and the surface plasmon excitation layer is in contact with the cladding through the depression.

4. The fiber-optic surface plasmon resonance sensor according to claim 3, wherein the distance between the core and the surface plasmon excitation layer is determined such that surface plasmons in the surface plasmon excitation layer can be excited by incident light which is propagated through the core and satisfies the resonance condition.

5. The fiber-optic surface plasmon resonance sensor according to claim 1, wherein the depression is formed on a surface in a direction perpendicular to the length direction of the optical fiber.

6. The fiber-optic surface plasmon resonance sensor according to claim 5, wherein the depression is formed with an annular shape along the surface of the optical fiber.

7. The fiber-optic surface plasmon resonance sensor according to claim 1, wherein the optical fiber comprises a first end at which incident light is incident through the core, and a second end opposite to the first end, and the surface plasmon resonance sensor further comprises a reflective layer which is provided at the second end and reflects the incident light.

8. The fiber-optic surface plasmon resonance sensor according to claim 7, wherein the reflective layer is spaced apart from the surface plasmon excitation layer along the length direction of the optical fiber.

9. The fiber-optic surface plasmon resonance sensor according to claim 7, wherein the reflective layer is in contact with the surface plasmon excitation layer.

10. The fiber-optic surface plasmon resonance sensor according to claim 1, wherein the thickness of the optical waveguide layer is determined based on the wavelength of incident light incident to the core.

11. The fiber-optic surface plasmon resonance sensor according to claim 1, wherein the first excitation layer comprises a metal, a semiconductor, a transparent conducting oxide, a carbon material, a chalcogenide material or a dielectric material.

12. The fiber-optic surface plasmon resonance sensor according to claim 1, wherein the second excitation layer comprises a metal, a semiconductor, a transparent conducting oxide, a carbon material or a chalcogenide material.

13. The fiber-optic surface plasmon resonance sensor according to claim 1, wherein the optical waveguide layer comprises a material which is optically transparent at the wavelength of the incident light incident to the core.

14. The fiber-optic surface plasmon resonance sensor according to claim 1, which further comprises a buffer layer provided between the optical fiber and the first excitation layer.

15. The fiber-optic surface plasmon resonance sensor according to claim 1, which further comprises an interface adhesion layer provided between the optical fiber and the first excitation layer.

16. The fiber-optic surface plasmon resonance sensor according to claim 1, which further comprises a sensing layer provided on the second excitation layer.

17. The fiber-optic surface plasmon resonance sensor according to claim 1, wherein the incident light incident to the core comprises at least one of a p-polarized component and an s-polarized component, and
wherein at least one of the position of at least one surface plasmon resonance mode wavelength due to the p-polarized component, the separation between surface plasmon resonance mode wavelengths of the at least one surface plasmon resonance mode wavelength, and the separation between the at least one surface plasmon resonance mode wavelength and an optical waveguide mode wavelength due to the s-polarized component is determined based on the material or thickness of the first excitation layer and the second excitation layer.

18. A sensing method comprising:
entering incident light through a core of an optical fiber comprising the core, a cladding surrounding the core, a depression, and a surface plasmon excitation layer on the depression, the surface plasmon excitation layer comprising a first excitation layer, a second excitation layer and an optical waveguide layer between the first excitation layer and the second excitation layer, the optical waveguide layer being a single layer;
coupling the incident light into the optical waveguide layer in optical waveguide mode;
exciting a surface plasmon wave in the surface plasmon excitation layer by the incident light coupled into the optical waveguide layer; and
detecting an analyte in contact with the surface plasmon excitation layer by measuring light exit from the optical fiber.

19. The sensing method according to claim 18, wherein the incident light comprises at least one of a p-polarized component and an s-polarized component.

20. The sensing method according to claim 19, wherein said coupling the incident light into the optical waveguide layer comprises coupling the s-polarized component into the optical waveguide layer.

21. The sensing method according to claim 19, wherein said detecting the analyte comprises removing a noise signal by comparing a signal due to the p-polarized component and a signal due to the s-polarized component from the exit light.

22. The sensing method according to claim 19, which further comprises controlling at least one of the position of at least one surface plasmon resonance mode wavelength due to the p-polarized component, the separation between surface plasmon resonance mode wavelengths of the at least one surface plasmon resonance mode wavelength, and the separation between the at least one surface plasmon resonance mode wavelength and an optical waveguide mode wavelength due to the s-polarized component by controlling the material or thickness of the first excitation layer and the second excitation layer.

23. The sensing method according to claim 18, further comprising:
tuning a surface plasmon resonance wavelength by controlling a thickness of the optical waveguide layer.

24. The fiber-optic surface plasmon resonance sensor according to claim 1, wherein the optical waveguide layer has a thickness such that the sensor has a plurality of surface plasmon resonance modes.

* * * * *